United States Patent [19]
Cooper

[11] Patent Number: 5,986,117
[45] Date of Patent: Nov. 16, 1999

[54] PROCESS FOR THE PREPARATION OF FATTY ACID-ESTERIFIED PROPOXYLATED GLYCERIN

[75] Inventor: Charles F. Cooper, Paoli, Pa.

[73] Assignee: Arco Chemical Technology, L.P., Greenville, Del.

[21] Appl. No.: 08/878,347

[22] Filed: Jun. 18, 1997

Related U.S. Application Data

[63] Continuation of application No. 08/731,507, Oct. 16, 1996, abandoned, which is a continuation of application No. 08/327,260, Oct. 21, 1994, abandoned.

[51] Int. Cl.$^6$ ........................................................ C11B 1/00
[52] U.S. Cl. .......................... 554/168; 554/149; 554/167; 554/169
[58] Field of Search ..................................... 554/167, 168, 554/169, 149

[56] References Cited

U.S. PATENT DOCUMENTS

| | | | |
|---|---|---|---|
| 5,175,323 | 12/1992 | Cooper | 554/164 |
| 5,304,665 | 4/1994 | Cooper | 554/149 |
| 5,399,728 | 3/1995 | Cooper | 554/149 |

FOREIGN PATENT DOCUMENTS 847517   2/1957   United Kingdom .

*Primary Examiner*—Deborah D Carr
*Attorney, Agent, or Firm*—Stephen D. Harper; William C. Long

[57] ABSTRACT

A convenient method of obtaining useful esterified propoxylated glycerin fat substitutes from readily available triglycerides such as fats and oil is provided wherein a triglyceride is reacted with a propoxylated glycerin under conditions effective to remove glycerin during such reaction.

16 Claims, No Drawings

5,986,117

PROCESS FOR THE PREPARATION OF FATTY ACID-ESTERIFIED PROPOXYLATED GLYCERIN

This is a continuation, of Application Ser. No. 08/731,507, filed Oct. 16, 1996, now abandoned, which is a continuation of Application Ser. No. 08/327,260, filed Oct. 21 1994, now abandoned.

FIELD OF THE INVENTION

This invention relates to methods for obtaining propoxylated glycerins esterified with fatty acids from triglycerides such as conventional fats and oils. The products obtained are useful reduced calorie fat substitutes.

BACKGROUND OF THE INVENTION

A wide variety of substances have been proposed for use as fat substitutes in food compositions. The chemical structures of such substances are selected such that they are more resistant to breakdown by the metabolic processes of the human digestive system which normally occur upon ingestion of conventional triglyceride lipids. Because of their increased resistance to digestion and absorption, the number of calories per gram available from the fat substitutes is considerably reduced as compared to common vegetable oils, animal fats, and other lipids. The use of such substances thus enables the preparation of reduced calorie food compositions useful in the control of body weight.

U.S. Pat. No. 4,861,613 describes one class of particularly useful fat substitutes wherein a polyol such as glycerin is alkoxylated with an epoxide such as propylene oxide and then esterified with any of a number of fatty acids or fatty acid equivalents to form an esterified alkoxylated polyol. Generally speaking, it is desirable to accomplish nearly complete esterification (i.e., to react at least 90% of the hydroxyl groups of the alkoxylated polyol intermediate with fatty acid). These substances have the physical and organoleptic properties of conventional triglyceride lipids, yet are significantly lower in available (absorbed) calories than edible oils owing to their pronounced resistance towards pancreatic lipase enzymatic hydrolysis. The thermal and oxidative stability of the esterified alkoxylated polyols renders them especially suitable for use in the preparation of reduced calorie food compositions requiring exposure to high temperatures.

The methods developed to date for the preparation of esterified alkoxylated polyol fat substitutes of this type have typically required multi-step procedures when a naturally occurring triglyceride is to be utilized as the source of the long chain ester groups incorporated into the esterified alkoxylated polyol. The triglyceride is first hydrolytically split into glycerin (which may be employed as the polyol component) and a mixture of fatty acids. The fatty acids (after separation from the glycerin) may be used directly without further modification as described in U.S. Pat. No. 4,983,329. Alternatively, the fatty acids prior to use in an esterification reaction with an alkoxylated polyol may be converted into $C_1$-$C_4$ alkyl esters (as described in U.S. Pat. No. 5,175,232) or fatty acid halides (as described in U.S. Pat. No. 4,861,613). The alkoxylated polyol must first be prepared by reacting an epoxide with a polyol such as glycerin, sugar alcohol, glycoside, monosaccharide, disaccharide or other organic compound having two or more hydroxy groups. While such multi-step procedures work well and afford esterified alkoxylated polyols suitable for use as fat substitutes, the number of steps involved, including both synthesis and purification steps, renders these substances considerably more costly than the triglycerides on which they are based. Since the esterified alkoxylated polyol is intended to entirely or substantially replace conventional high caloric triglycerides in food compositions and since certain types of food compositions will normally contain high levels of fat or oil, it is apparent there exists a great need for improved processes whereby the manufacturing cost of esterified alkoxylated polyols may be substantially reduced.

SUMMARY OF THE INVENTION

This invention provides a method for producing a fatty acid-esterified propoxylated glycerin comprising reacting a propoxylated glycerin with a triglyceride in a reaction zone to form glycerin and the fatty acid-esterified propoxylated glycerin, wherein the glycerin is removed from the reaction zone during said reacting.

DETAILED DESCRIPTION OF THE INVENTION

The triglyceride component which is necessary for the practice of this invention may be any synthetic or naturally-occurring fatty acid triester of glycerin. Such substances will typically correspond to the general structure

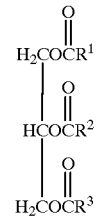

wherein $R^1$, $R^2$ and $R^3$ are the same or different and are $C_5$-$C_{23}$ saturated or unsaturated, linear or branched hydrocarbyl groups (i.e., moieties comprised of carbon and hydrogen atoms). The glycerin may be esterified, for example, with any $C_6$-$C_{24}$ fatty acid such as caproic acid, caprylic acid, pelargonic acid, capric acid, undecylic acid, lauric acid, palmitic acid, margeric acid, stearic acid, nonadecylic acid, arachidic acid, behenic acid, lignoceric acid, lauroleic acids, myristoleic acids, palmitoleic acids, oleic acid, elaidic acid, godoleic acid, gondoic acids, cetoleic acid, linoleic acid, linolenic acid, eleostearic acids, and mixtures thereof. Esterification with $C_{16}$-$C_{24}$ fatty acids is especially preferred, since such fatty acids will have a reduced tendency to be taken overhead when the glycerin is removed from the reaction zone by distillation. Suitable triglycerides are preferably obtained from edible oils and fats including, for example, the triesters of glycerin obtained from natural lipids such as cottonseed oil, soybean oil, peanut oil, olive oil, safflower oil, rapeseed oil (preferably, low erucic rapeseed oil, which is also referred to as canola oil, or fully hydrogenated high erucic rapeseed oil), fish oils, sunflower oil, palm oil, palm kernel oil, tallow, lard, coconut oil, sesame oil, corn oil, and fully or partially hydrogenated derivatives thereof.

Propoxylated glycerins suitable for reaction with the triglyceride are well-known in the art and include those substances obtainable by reacting propylene oxide with glycerin. For the purpose of obtaining a reduced calorie fat substitute, from 3 to 18 moles of propylene oxide per mole of glycerin is preferably reacted. Such reaction may, if so desired, be catalyzed by any of the substances known to catalyze the ring-opening addition of epoxides onto the hydroxyl groups of a poly alcohol (polyol) including, for example, basic catalysts (e.g., KOH), acidic catalysts (e.g., $BF_3$.etherate), and coordination catalysts. In one desirable embodiment of the invention, the same catalyst used for glycerin propoxylation is also employed to catalyze the reaction of the propoxylated glycerin with the triglyceride. The need to remove the propoxylation catalyst prior to esterification is thereby avoided.

The propoxylated glycerin will in a preferred embodiment correspond to the formula

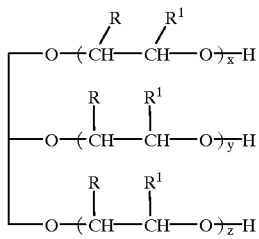

wherein R and $R^1$ are different and are selected from hydrogen and methyl and x, y and z are the same or different and are 0 or an integer of from 1 to 18, wherein x+y+z is from 3–18.

While the triglyceride and the propoxylated glycerin may be reacted in any proportion, it will generally be preferred to use a propoxylated glycerin: triglyceride molar ratio of from 0.8:1 to 1.2:1 where a fatty acid-esterified propoxylated glycerin having a relatively high degree of esterification (average number of ester groups per molecule) is desired. The degree of esterification is preferably 80% or greater (i.e., at least 80% of the hydroxy groups in the starting propoxylated glycerin have been esterified). The extent of esterification may be readily monitored by standard analytical methods including, for example, hydroxyl number. Typically, the esterified propoxylated glycerins obtained using the process of this invention will have hydroxyl numbers of less than 50 mg KOH per gram. The instant process is capable of producing esterified propoxylated glycerin having hydroxyl numbers approaching 0 (i.e., products which are completely esterified).

In order to drive the propoxylated glycerin esterification to a desirable level of completion, glycerin is removed from the reaction zone, preferably within a relatively short period of time after it is generated as an esterification coproduct so as to avoid high glycerin concentrations. Preferably, the free glycerin concentration is maintained below 1% (more preferably, below 0.5%) by weight. Such removal may be readily accomplished by distillative means as the glycerin, while fairly high boiling, has a lower boiling point than the other components of the reaction mixture (e.g., triglyceride, propoxylated glycerin). Removal of glycerin may be expedited through the application of vacuum, i.e., by conducting the reaction under subatmospheric (reduced) pressure. The reaction is desirably carried out at a pressure of from about 0.1 to about 200 mm Hg (preferably, from about 1 to 50 mm Hg). Sparging of a stripping agent such as nitrogen or other inert gas or a volatile hydrocarbon may also be utilized, either alone or in combination with the application of vacuum. The stripping agent, if any, may be separated from the glycerin and recycled. Substances which form low boiling azeotropes with glycerin may also be employed. In one embodiment of the invention, the stripping agent used is steam. With short contact time, ester hydrolysis is minimized.

The removal conditions are selected such that essentially only the glycerin is taken overhead; the reactants, intermediates and the fatty acid-esterified propoxylated glycerin product are substantially retained in the reaction zone.

Other removal means are also feasible, including, for example, membrane separation techniques wherein a glycerin-permeable membrane is utilized or extraction methods wherein glycerin is preferentially extracted into an aqueous phase.

The glycerin which is removed from the reaction zone may readily be recycled for use in the preparation of additional quantities of fatty acid-esterified propoxylated glycerin. For example, the recovered glycerin may be propoxylated with propylene oxide to yield the propoxylated glycerin utilized as one of the reactants in the process of this invention.

A catalyst may be present within the reaction zone to increase the rate of reaction between the triglyceride and the propoxylated glycerin. Any substance capable of catalyzing interesterification or transesterification can be used for such purpose, including acidic as well as basic catalysts. Preferably, the catalyst is basic in character and may be selected from among those materials which are alkali metals, alkali metal compounds, alkaline earth metals, alkaline earth metal compounds, or ammonium compounds since such substances exhibit high activity, tend to cause few problems with the formation of undesired by-products or impurities, may be readily removed by conventional methods once esterification of the propoxylated glycerin is accomplished, are relatively non-volatile (thus permitting the selective removal of glycerin by distillative means from the reaction mixture) and do not generally raise any unusual concerns with respect to toxicity or other harmful effects if trace amounts remain in the esterified propoxylated glycerin product. Illustrative alkali metal, alkaline earth metal, or ammonium compounds which can be utilized include, but are not limited to, ammonium, sodium, lithium, potassium, calcium, barium, or magnesium hydroxides, alkoxides (e.g., methoxides, ethoxides, propoxides, or butoxides, salts of glycerin or other polyols such as diols, triols, tetrols, alkoxylated glycerin, other polyhydric substances), amides, carbonates, bicarbonates, hydrides, oxides, amides, carboxylates (e.g., fatty acid salts), phosphates, borates, sulfates, and the like. Alkali metals such as sodium metal (which may be in the form of a dispersion) or a sodium-potassium alloy may be employed. Heterogeneous (insoluble) as well as homogeneous (soluble) catalysts are suitable for use. Basic ion exchange resins such as, for example, quaternary or tertiary amine-functionalized polystyrenic resins represent one class of heterogeneous catalysts suitable for deployment in the process of this invention. The amount of catalyst is not critical and the optimum concentration can be readily determined by routine experimentation. If the catalyst is an alkali metal or an alkali metal, alkaline earth metal, or ammonium compound, typically the catalyst concentration can suitably be in the range of from 0.01 to 3 weight percent based on the total combined weight of the triglyceride and the propoxylated glycerin. If the basic catalyst is heterogeneous in character, higher catalyst levels (e.g., up to 25 weight percent) may be preferred. If the catalyst is particularly reactive (air or moisture sensitive) or otherwise difficult to handle in pure form, it may be first suspended, dispersed, or dissolved in a suitable carrier or vehicle such as, for example, one or more of the reactants or products prior to use in the process. A catalyst pretreatment of this type will help protect the catalyst from deactivation and degradation and also ensure a uniform distribution of catalyst throughout the reaction mixture.

In a particularly desirable embodiment of the invention, crude propoxylated glycerin (i.e., propoxylated glycerin still containing the basic catalyst used for propoxylation) is used directly without intervening purification. Where the basic propoxylation catalyst is an alkali metal such as potassium, for example, the crude propoxylated glycerin will contain some proportion of the alkali metal salt of the propoxylated glycerin. The salt will effectively catalyze esterification of the propoxylated glycerin when reacted with the triglyceride. An intermediate propoxylation catalyst removal step thus is not needed. The reactants and catalyst are preferably well agitated or intimately mixed within the reaction zone so as to minimize reaction times, temperature fluctuations, and product heterogeneity.

The temperature at which the triglyceride and propoxylated glycerin are reacted is not critical, but should be selected so as to be sufficiently high to provide relatively rapid rates of propoxylated glycerin esterification and glycerin evolution, and yet not so high as to generate undesirable by-products. Typically, suitable temperatures will be in the range of from 50° C. to 30° C. When a catalyst and a reduced pressure are employed, it will be feasible to practice the process of this invention at a temperature of less than 200°C.

The reaction mixture is held at the selected temperature or within the selected temperature range for a period of time sufficiently long so as to accomplish the desired degree of propoxylated glycerin conversion, which will generally be at least 75% of the propoxylated glycerin charged (as measured by hydroxy group esterification) and more preferably is at least 90% of the propoxylated glycerin. Reaction times of from about 0.5 hours to 24 hours will typically suffice for this purpose, but will be dependent on variables such as triglyceride or propoxylated glycerin reactivity, temperature, catalyst concentration and activity and the like. Optimum reaction times may be readily determined by routine experimentation.

An important advantage of the instant process is that a solvent is not required, since the triglycerides and propoxylated glycerins suitable for use are typically free-flowing liquids at the reaction temperatures employed which are miscible with or soluble in each other.

The reaction is most preferably carried out under an inert (oxygen-free) atmosphere in the absence of active hydrogen-containing compounds other than the propoxylated glycerin as the presence of such substances may detrimentally effect the quality of the partially esterified alkoxylated polyol.

The process may be conducted in a continuous, semi-continuous, or batch manner using any appropriately configured reactor capable of heating and mixing the reactor contents. Although all of the reactants may be combined together at once when performing the reaction, it may under certain conditions be desirable to add one reactant to the other in an incremental or staged fashion.

When the reaction of the triglyceride and propoxylated glycerin has proceeded to the extent desired to form the esterified propoxylated glycerin, any catalyst present may (if desired) be removed by an appropriate method such as extraction, filtration, neutralization, precipitation, or absorption. For example, where a basic catalyst is used, the reaction product can be contacted with a particulate absorbent such as magnesium silicate or aluminum silicate at an appropriate temperature (typically, 50° C. to 150° C. so as to absorb the catalyst onto the absorbent and then filtered. Small amounts of water may be added so as to enhance absorption efficiency. Alternatively, the reaction product can be treated with an acid such as a mineral acid (e.g., hydrochloric acid, sulfuric acid, phosphoric acid) or an organic acid (e.g., acetic acid, oxalic acid, citric acid, tartaric acid) so as to form a precipitate which can be removed by filtration. Treatment with an appropriate ion exchange resin or extraction with water, dilute aqueous acid, or a polar solvent such as methanol or the like may also be utilized.

The fatty acid-esterified propoxylated glycerin produced by the process of this invention can be additionally purified or treated so as to render it more suitable for use in food compositions using any of the techniques known in the art for refining natural vegetable or animals oils and fats. Such techniques include, but are not limited to, degumming, bleaching, filtration, deodorization (including steam deodorization), hydrogenation, dewaxing, and the like. Various additives such as stabilizers, anti-oxidants, vitamins and so forth can also be incorporated into the esterified propoxylated glycerin.

Esterified propoxylated glycerins produced in accordance with this invention can replace, in full or in part, conventional edible oils or fats in a cooking oil, frying oil, salad oil, or shortening, for example. Additional uses include combining the reduced calorie fat substitute with other foodstuff ingredients to form foods such as frozen deserts (e.g., sherbet, ice cream, frozen yogurt, milk shakes), baked goods (cakes, doughnuts, muffins, brownies, breads, pies, rolls, pastries, cookies, biscuits, crackers), nut butters (peanut butter), dairy products (margarine, sour cream, coffee lighteners, cheese, cheese spreads, flavored dips, filled cream, filled milk), mayonnaise, salad dressing, savory snacks (potato chips, corn chips, cheese puffs, pretzels), fried foods (fried poultry, fritters, fried pies, fried vegetables such as french fried potatoes, fried fish), reformed and comminuted meats (lunch meats, sausage, hot dogs, hamburger), pet food, meat and egg substitutes or extenders, whipped toppings, gravies and other sauces, frosting, fillings, icings, cocoa butter replacements or blends, candies (especially those normally containing fatty ingredients such as chocolate or peanut butter), soups and dry baking mixes (for muffins, cakes, pancakes, waffles, brownies, and the like). Owing to the fat-like properties and stability of the esterified propoxylated glycerins, minimum reformulation of standard foods will generally be required. The viscosity, melting profile, yield point, hardness, thixotropic area, liquid/solid stability, solid fat index, and other physical properties of the reduced calorie fat substitute are preferably selected by manipulation of the chemical structures and relative proportions of the individual starting materials of the process such that the product mimics as closely as possible the analogous properties of the conventional triglyceride being replaced.

Illustrative ingredients which may be used in combination with the esterified propoxylated glycerins obtainable by practice of this invention include carbohydrates (flour, starches, sugars, celluloses, polydextrose or other bulking agents), edible lipids (triglycerides), proteins (from animal or vegetable sources) vitamins, antioxidants, emulsifiers, thickeners, preservatives, colorants, flavors, fragrances, sugar substitutes (saccharin, aspartame, sucralose, cyclamates, and the like), other fat substitutes or fat mimetics (for example, sucrose polyester, salatrim, or caprenin), water, milk, spices, eggs and the like. Oil-in-water or water-in-oil emulsions can be readily prepared by combining water, the reduced calorie fat substitute, and (optionally) other ingredients such as emulsifiers. The reduced calorie fat substitutes produced using this invention are particularly suitable for the preparation of foods requiring exposure to elevated temperatures. Unlike other proposed fat substitutes such as proteinaceous amcrocolliods or certain polysaccharide-based substances requiring water to render them fat-like in texture, the esterified propoxylated glycerins produced by this invention are exceptionally stable thermally and do not readily decompose or lose their fat-like properties when heated. The compositions thus may readily be utilized in deep fat frying applications to prepare fried foods such as savory snacks, fried chicken, fried fish, french fries, and the like since they will function as effective heat transfer media (that is, they will transmit heat rapidly and uniformly to the food being fried and also provide crispness).

From the foregoing description, one skilled in the art can readily ascertain the essential characteristics of this invention and, without departing from the spirit and scope thereof, can make various changes and modifications of the invention to adapt it to various usages, conditions, and embodiments.

The following examples further illustrate the process of this invention, but are not limitative of the invention in any manner whatsoever.

EXAMPLE 1

Propoxylated glycerin (556 parts by weight; containing ca. 8 moles of propylene oxide per mole of glycerin) containing 0.5% propoxylated glycerin alkoxide (as potassium) is heated to 175° C. under reduced pressure. Nitrogen sparging is introduced beneath the surface of the propoxylated glycerin. Simultaneously, soybean oil (875 parts) is added as a separate stream. Co-product glycerin is removed overhead. When glycerin evolution ceases, the resulting product is steam deodorized to afford a fatty acid-esterified propoxylated glycerin suitable for use as a reduced calorie fat substitute.

I claim:

1. A method for producing a fatty acid-esterified propoxylated glycerin comprising reacting a propoxylated glycerin with a triglyceride at a molar ratio of propoxylated glycerin:triglyceride of from 0.8:1 to 1.2:1 in the presence of a catalyst in a reaction zone at a temperature of from 50° C. to 275° C. to form glycerin and the fatty acid-esterified propoxylated glycerin, wherein the glycerin is continuously removed from the reaction zone during said reacting by distillation and said reacting is continued for a time sufficient to achieve a degree of esterification in the fatty acid-esterified propoxylated glycerin of at least 80%.

2. The method of claim 1 wherein the catalyst is an alkali metal catalyst.

3. The method of claim 1 wherein a stripping agent selected from steam, inert gases, and volatile hydrocarbons is sparged into the reaction zone during said reacting.

4. The method of claim 1 wherein the catalyst is an alkali metal catalyst and the propoxylated glycerin is derived from propoxylating glycerin with from 3 to 18 equivalents propylene oxide per equivalent of glycerin in the presence of the alkali metal catalyst.

5. The method of claim 1 wherein after said reacting the fatty acid-esterified propoxylated glycerin is steam deodorized.

6. The method of claim 1 wherein after said reacting the catalyst is removed from the fatty acid-esterified propoxylated glycerin.

7. The method of claim 1 wherein the glycerin is recycled for use in preparing a propoxylated glycerin.

8. The method of claim 1 wherein the triglyceride is derived from a lipid selected from the group consisting of tallow, soybean oil, cottonseed oil, coconut oil, palm kernel oil, corn oil, fish oil, lard, butter fat, olive oil, palm oil, peanut oil, safflower seed oil, cocoa butter, sesame oil, rapeseed oil, canola oil, sunflower oil, hydrogenated derivatives, and mixtures thereof.

9. The method of claim 1 wherein the fatty acid-esterified propoxylated glycerin has a hydroxyl number of less than 50 mg KOH per gram.

10. The method of claim 1 wherein the glycerin concentration in the reaction zone is maintained below 1% by weight.

11. The method of claim 1 wherein said time is from 0.5 to 24 hours.

12. The method of claim 1 wherein said reacting time is performed in the absence of a solvent.

13. The method of claim 1 wherein the catalyst is a base catalyst.

14. The method of claim 1 wherein the catalyst is a basic ion exchange resin.

15. The method of claim 1 wherein said reacting is performed at subatmospheric pressure.

16. A method for producing a fatty acid-esterified propoxylated glycerin comprising the steps of (a) propoxylating glycerin with from 3 to 18 equivalents propylene oxide per equivalent of glycerin in the presence of an alkali metal catalyst to form a propoxylated glycerin containing alkali metal catalyst;

(b) reacting the propoxylated glycerin containing alkali metal catalyst with a triglyceride at a molar ratio of propoxylated glycerin:triglyceride of from 0.8:1 to 1.2:1 in a reaction zone at a temperature of from 50° C. to 275° C. to form glycerin and the fatty acid-esterified propoxylated glycerin, wherein the glycerin is continuously removed from the reaction zone during said reacting by distillation and said reacting is continued for a time sufficient to achieve a degree of esterification in the fatty acid-esterified propoxylated glycerin of at least 80%; and (c) recycling the glycerin removed in step (b) for use in step (a).

* * * * *